United States Patent
Lambert et al.

(10) Patent No.: US 10,551,305 B2
(45) Date of Patent: Feb. 4, 2020

(54) METHOD FOR DETERMINING THE ORIGIN OF A MIXTURE OF CONSTITUENTS BY SPECTRAL ANALYSIS

(71) Applicant: TOPNIR SYSTEMS SAS, Aix en Provence (FR)

(72) Inventors: Didier Lambert, Bernos Beaulac (FR); Claude Saint Martin, Pelissane (FR); Miguel Sanchez, Lavera (FR); Bernard Ribero, Peyrolles en Provence (FR)

(73) Assignee: TOPNIR SYSTEMS SAS, Aix en Provence (FR)

( * ) Notice: Subject to any disclaimer, the term of this patent is extended or adjusted under 35 U.S.C. 154(b) by 4 days.

(21) Appl. No.: 15/523,318

(22) PCT Filed: Oct. 27, 2015

(86) PCT No.: PCT/EP2015/074876
§ 371 (c)(1),
(2) Date: Apr. 28, 2017

(87) PCT Pub. No.: WO2016/066646
PCT Pub. Date: May 6, 2016

(65) Prior Publication Data
US 2017/0336321 A1  Nov. 23, 2017

(30) Foreign Application Priority Data
Oct. 30, 2014 (EP) .................................. 14290326

(51) Int. Cl.
*G01N 21/359* (2014.01)
*G01N 21/3504* (2014.01)
(Continued)

(52) U.S. Cl.
CPC ....... *G01N 21/359* (2013.01); *G01N 21/3504* (2013.01); *G01N 21/3577* (2013.01);
(Continued)

(58) Field of Classification Search
CPC ............. G01N 21/359; G01N 21/3504; G01N 21/3577; G01N 33/2829; G01N 33/2835;
(Continued)

(56) References Cited

U.S. PATENT DOCUMENTS 4,642,778 A * 2/1987 Hieftje ...................... G01J 3/28
702/23
5,301,125 A * 4/1994 Chimenti ............... G01N 21/25
208/28
(Continued)

FOREIGN PATENT DOCUMENTS

FR  2619624 A1  2/1989
WO  2011/073855  6/2011

OTHER PUBLICATIONS

International Search Report and Written Opinion dated Feb. 4, 2016 in PCT Application PCT/EP2015/074876.

*Primary Examiner* — Christine S. Kim
(74) *Attorney, Agent, or Firm* — Maschoff Brennan

(57) ABSTRACT

The invention relates to a method for determining the origin of a mixture of constituents by spectral analysis. The invention especially relates to a method for determining the concentration and origin of raw gases and/or crude oils in a mixing zone following mixing by the transport of said raw gases and/or crude oils that come from at least two different sources of extraction, said method comprising a specific spectral analysis.

7 Claims, 10 Drawing Sheets

(51) Int. Cl.
*G01N 21/3577* (2014.01)
*G01N 33/38* (2006.01)
*G01V 8/10* (2006.01)
*G01N 21/17* (2006.01)
*G01N 33/28* (2006.01)

(52) U.S. Cl.
CPC ........... *G01N 33/2835* (2013.01); *G01V 8/10* (2013.01); *G01N 2021/1748* (2013.01); *G01N 2201/12* (2013.01)

(58) Field of Classification Search
CPC ....... G01N 2021/1748; G01N 2201/12; G01V 8/10
See application file for complete search history.

(56) References Cited

U.S. PATENT DOCUMENTS

| | | | |
|---|---|---|---|
| 5,717,209 A | 2/1998 | Bigman et al. | |
| 6,070,128 A | 5/2000 | Descales et al. | |
| 6,087,662 A | 7/2000 | Wilt et al. | |
| 9,678,002 B2* | 6/2017 | Miao | G01N 21/3577 |
| 2004/0033617 A1 | 2/2004 | Sonbul | |
| 2009/0216463 A1* | 8/2009 | Xie | G01N 21/314 |
| | | | 702/24 |
| 2010/0116991 A1 | 5/2010 | Saul et al. | |
| 2010/0307740 A1 | 12/2010 | Abivin et al. | |

* cited by examiner

SPECTRAL DATABANK A

FIGURE 2

| VGS Wavelength | W1 | W2 | W3 | W4 | W5 | W6 | W7 | W8 | W9 |
|---|---|---|---|---|---|---|---|---|---|
| | 1.5243E-07 | 5.98E-06 | 5.43E-06 | 9.39E-06 | 1.38E-05 | 2.07E-05 | 2.62E-05 | 3.04E-05 | 4.14E-05 |
| | 1.1204E-07 | 6.81E-06 | 5.33E-06 | 9.54E-06 | 1.46E-05 | 2.15E-05 | 2.69E-05 | 3.11E-05 | 4.18E-05 |
| | 1.5575E-06 | 4.53E-06 | 6.07E-06 | 9.07E-06 | 1.45E-05 | 2.07E-05 | 2.6E-05 | 3.13E-05 | 4.12E-05 |
| | 4.1509E-08 | 6.65E-06 | 5.33E-06 | 9.63E-06 | 1.45E-05 | 2.09E-05 | 2.62E-05 | 3.12E-05 | 4.14E-05 |
| | 1.2844E-07 | 6.52E-06 | 5.19E-06 | 9.68E-06 | 1.46E-05 | 2.21E-05 | 2.7E-05 | 3.08E-05 | 4.2E-05 |
| | 1.5268E-06 | 4.24E-06 | 6.16E-06 | 8.66E-06 | 1.36E-05 | 1.97E-05 | 2.57E-05 | 3.07E-05 | 4.05E-05 |
| | 1.4570E-06 | 4.02E-06 | 6.06E-06 | 9.18E-06 | 1.47E-05 | 2.04E-05 | 2.63E-05 | 3.14E-05 | 4.1E-05 |
| | 1.8449E-06 | 4.52E-06 | 5.79E-06 | 8.99E-06 | 1.43E-05 | 2.02E-05 | 2.62E-05 | 3.16E-05 | 4.17E-05 |
| | 1.7304E-06 | 4.4E-06 | 6.12E-06 | 8.94E-06 | 1.42E-05 | 2.04E-05 | 2.63E-05 | 3.11E-05 | 4.07E-05 |
| | 1.1190E-06 | 3.85E-06 | 6.37E-06 | 9.31E-06 | 1.43E-05 | 2.08E-05 | 2.59E-05 | 3.07E-05 | 4.07E-05 |
| VGSm | 9.6703E-07 | 5.15E-06 | 5.79E-06 | 9.24E-06 | 1.43E-05 | 2.07E-05 | 2.63E-05 | 3.11E-05 | 4.12E-05 |
| σ | 7.6254E-07 | 1.19E-06 | 4.27E-07 | 3.31E-07 | 3.79E-07 | 6.75E-07 | 4.21E-07 | 3.79E-07 | 4.99E-07 |
| $\frac{\sigma}{m} \times 100$ | 78.85 | 23.09 | 7.38 | 3.58 | 2.65 | 3.26 | 1.60 | 1.22 | 1.21 |

SPECTRAL DATABANK B

| Absorbency % Weight | Germ 1 | Germ 2 | Germ 3 | 4764 | 4760 | 4756 | 4752 | 4748 | 4744 | 4740 | 4736 |
|---|---|---|---|---|---|---|---|---|---|---|---|
| Name | | | | | | | | | | | |
| A0000001 | | | | 7.78E-06 | 1.29E-05 | 1.88E-05 | 2.42E-05 | 3.16E-05 | 4.42E-05 | 6.18E-05 | 8.01E-05 |
| A0000002 | | | | 8.08E-06 | 1.37E-05 | 1.96E-05 | 2.5E-05 | 3.18E-05 | 4.46E-05 | 6.09E-05 | 7.91E-05 |
| A0000003 | | | | 8.78E-06 | 1.52E-05 | 2.23E-05 | 2.97E-05 | 3.99E-05 | 5.53E-05 | 7.54E-05 | 9.68E-05 |
| A0000004 | | | | 7.46E-06 | 1.26E-05 | 1.81E-05 | 2.47E-05 | 3.29E-05 | 4.71E-05 | 6.55E-05 | 8.47E-05 |
| A0000005 | | | | 1.01E-05 | 1.59E-05 | 2.39E-05 | 3.28E-05 | 4.34E-05 | 5.93E-05 | 8.08E-05 | 0.000104 |
| A0000006 | | | | 5.49E-06 | 9.2E-06 | 1.41E-05 | 1.88E-05 | 2.54E-05 | 3.62E-05 | 5.18E-05 | 6.97E-05 |
| A0000007 | | | | 7.14E-06 | 1.21E-05 | 1.86E-05 | 2.41E-05 | 3.27E-05 | 4.63E-05 | 6.32E-05 | 8.49E-05 |
| A0000008 | | | | 1.03E-05 | 1.64E-05 | 2.4E-05 | 3.28E-05 | 4.39E-05 | 6.13E-05 | 8.42E-05 | 0.000109 |
| A0000009 | | | | 8.25E-06 | 1.15E-05 | 1.4E-05 | 1.62E-05 | 1.99E-05 | 2.56E-05 | 3.56E-05 | 4.94E-05 |
| 12G022 | 0.564 | A0000003 | A0000006 | 7.35E-06 | 1.26E-05 | 1.88E-05 | 2.49E-05 | 3.36E-05 | 4.7E-05 | 6.51E-05 | 8.5E-05 |
| | 0.436 | | | | | | | | | | |
| 12G011 | 0.654 | A0000009 | A0000001 | 8.09E-06 | 1.2E-05 | 1.57E-05 | 1.9E-05 | 2.4E-05 | 3.21E-05 | 4.47E-05 | 6E-05 |
| | 0.346 | | | | | | | | | | |
| 12G036 | 0.44 | A0000008 | A0000004 | 8.69E-06 | 1.43E-05 | 2.07E-05 | 2.81E-05 | 3.77E-05 | 5.33E-05 | 7.38E-05 | 9.54E-05 |
| | 0.56 | | | | | | | | | | |
| 13G038 | 0.747 | A0000002 | A0000004 | 9.71E-06 | 1.57E-05 | 2.29E-05 | 3.06E-05 | 4.09E-05 | 5.7E-05 | 7.83E-05 | 0.000101 |
| | 0.258 | | | | | | | | | | |
| | -0.005 | | | | | | | | | | |
| 13G025 | 0.5825 | A0000008 | A0000005 | A0000003 | 1E-05 | 1.61E-05 | 2.38E-05 | 3.23E-05 | 4.33E-05 | 6E-05 | 8.22E-05 | 0.000106 |
| | 0.3020 | | | | | | | | | | |
| | 0.1155 | | | | | | | | | | |
| 13G019 | 0.094 | A0000004 | A0000005 | A0000007 | 7.43E-06 | 1.23E-05 | 1.81E-05 | 2.46E-05 | 3.28E-05 | 4.7E-05 | 6.54E-05 | 8.46E-05 |
| | -0.00047 | | | | | | | | | | |
| | 0.00647 | | | | | | | | | | |

BROADENED SPECTRAL DATABANK E

FIGURE 5

| Absorbency Name | Pole | Germ | % Weight | 4764 | 4760 | 4756 | 4752 | 4748 | 4744 | 4740 | 4736 | 4732 |
|---|---|---|---|---|---|---|---|---|---|---|---|---|
| A0000001 | | | | 7.78E-06 | 1.29E-05 | 1.88E-05 | 2.42E-05 | 3.16E-05 | 4.42E-05 | 6.18E-05 | 8.01E-05 | 9.88E-05 |
| A0000002 | | | | 8.08E-06 | 1.37E-05 | 1.96E-05 | 2.5E-05 | 3.18E-05 | 4.46E-05 | 6.09E-05 | 7.91E-05 | 9.8E-05 |
| A0000003 | | | | 8.78E-06 | 1.52E-05 | 2.23E-05 | 2.97E-05 | 3.99E-05 | 5.53E-05 | 7.54E-05 | 9.68E-05 | 0.000118 |
| A0000004 | | | | 7.46E-06 | 1.26E-05 | 1.81E-05 | 2.47E-05 | 3.29E-05 | 4.71E-05 | 6.55E-05 | 8.47E-05 | 0.000104 |
| A0000005 | | | | 1.01E-05 | 1.59E-05 | 2.39E-05 | 3.28E-05 | 4.34E-05 | 5.93E-05 | 8.08E-05 | 0.000104 | 0.000128 |
| A0000006 | | | | 5.49E-06 | 9.2E-06 | 1.41E-05 | 1.88E-05 | 2.54E-05 | 3.62E-05 | 5.18E-05 | 6.97E-05 | 8.68E-05 |
| A0000007 | | | | 7.14E-06 | 1.21E-05 | 1.86E-05 | 2.41E-05 | 3.27E-05 | 4.63E-05 | 6.52E-05 | 8.49E-05 | 0.000104 |
| A0000008 | | | | 1.03E-05 | 1.64E-05 | 2.4E-05 | 3.26E-05 | 4.39E-05 | 6.13E-05 | 8.42E-05 | 0.000109 | 0.000136 |
| A0000009 | | | | 8.25E-06 | 1.15E-05 | 1.4E-05 | 1.62E-05 | 1.99E-05 | 2.56E-05 | 3.56E-05 | 4.94E-05 | 6.62E-05 |
| MEG001 | PAL054 | A0000009 | 0.15 | 4.45E-06 | 7.13E-06 | 9.35E-06 | 1.12E-05 | 1.44E-05 | 1.95E-05 | 2.84E-05 | 4.08E-05 | 5.62E-05 |
| MEG002 | PAL014 | A0000005 | -0.05 | 1.15E-05 | 1.78E-05 | 2.63E-05 | 3.57E-05 | 4.69E-05 | 6.36E-05 | 8.61E-05 | 0.00011 | 0.000135 |
| MEG003 | PAL035 | A0000008 | 0.08 | 8.11E-06 | 1.37E-05 | 2.06E-05 | 2.84E-05 | 3.88E-05 | 5.48E-05 | 7.6E-05 | 9.89E-05 | 0.000224 |
| MEG004 | PRF006 | A0000002 | 0.021655 | 8.65E-06 | 1.43E-05 | 2.03E-05 | 2.57E-05 | 3.26E-05 | 4.53E-05 | 6.16E-05 | 7.99E-05 | 9.88E-05 |
| MEG005 | PRF004 | A0000007 | -0.07268 | 4.86E-06 | 9.48E-06 | 1.56E-05 | 2.07E-05 | 2.94E-05 | 4.35E-05 | 6.29E-05 | 8.26E-05 | 0.000102 |
| MEG006 | PRF074 | A0000003 | 0.028752 | 9.54E-06 | 1.61E-05 | 2.33E-05 | 3.07E-05 | 4.07E-05 | 5.59E-05 | 7.58E-05 | 9.72E-05 | 0.000119 |

BROADENED SPECTRAL DATABANK EE

FIGURE 6

| Absorbency Name | Germ 1 | Germ 2 | Germ 3 | Pole % Weight | 4764 | 4760 | 4756 | 4752 | 4748 | 4744 | 4740 |
|---|---|---|---|---|---|---|---|---|---|---|---|
| A0000001 | | | | | 7.78E-06 | 1.29E-05 | 1.89E-05 | 2.42E-05 | 3.16E-05 | 4.43E-05 | 6.16E-05 |
| A0000002 | | | | | 8.08E-06 | 1.37E-05 | 1.96E-05 | 2.5E-05 | 3.18E-05 | 4.46E-05 | 6.09E-05 |
| A0000003 | | | | | 8.78E-06 | 1.52E-05 | 2.23E-05 | 2.97E-05 | 3.99E-05 | 5.53E-05 | 7.54E-05 |
| A0000004 | | | | | 7.46E-06 | 1.26E-05 | 1.81E-05 | 2.47E-05 | 3.29E-05 | 4.71E-05 | 6.55E-05 |
| A0000005 | | | | | 1.01E-05 | 1.59E-05 | 2.39E-05 | 3.18E-05 | 4.34E-05 | 5.93E-05 | 8.09E-05 |
| A0000006 | | | | | 5.49E-06 | 9.2E-06 | 1.41E-05 | 1.88E-05 | 2.54E-05 | 3.62E-05 | 5.18E-05 |
| A0000007 | | | | | 7.14E-06 | 1.22E-05 | 1.86E-05 | 2.41E-05 | 3.27E-05 | 4.63E-05 | 6.52E-05 |
| A0000008 | | | | | 1.03E-05 | 1.64E-05 | 2.4E-05 | 3.26E-05 | 4.39E-05 | 6.13E-05 | 8.42E-05 |
| A0000009 | | | | | 8.25E-06 | 1.15E-05 | 1.4E-05 | 1.62E-05 | 1.99E-05 | 2.56E-05 | 3.56E-05 |
| MEP001 | A0000002 | A0000006 | | 0 PAL021 0.56 / 0.34 / 0.1 0.304 / 0.646 / | 4.86E-06 | 8.85E-06 | 1.35E-05 | 1.9E-05 | 2.41E-05 | 3.54E-06 | 5.04E-05 |
| MEP002 | A0000005 | A0000003 | | 0 PRF028 0.05 1.1726 / -0.0926 | 1.05E-05 | 1.68E-05 | 2.43E-05 | 3.24E-05 | 4.26E-05 | 5.78E-05 | 7.8E-05 |
| MEP003 | A0000005 | A0000008 | | 0 PRF063 / -0.08 0.306 / -0.0530 / | 8.68E-06 | 1.44E-05 | 2.21E-05 | 3.1E-05 | 4.19E-05 | 5.78E-05 | 7.92E-05 |
| MEP004 | A0000006 | A0000009 | A0000002 | PAL037 0.647 / 0.1 0.6362 / 0.314 / | 4.89E-06 | 9.38E-06 | 1.46E-05 | 1.93E-05 | 2.55E-05 | 3.07E-05 | 5.17E-05 |
| MEP005 | A0000008 | A0000005 | A0000003 | PAL006 0.1198 / -0.04 0.273 / 0.4170 / | 1.11E-05 | 1.78E-05 | 2.56E-05 | 3.44E-05 | 4.59E-05 | 6.33E-05 | 8.63E-05 |
| MEP006 | A0000002 | A0000006 | A0000005 | PRF025 0.22 / 0.09 | 3.96E-06 | 1.52E-05 | 2.16E-05 | 2.8E-05 | 3.54E-05 | 4.75E-05 | 6.44E-05 |

BROADENED SPECTRAL DATABANK EEI

FIGURE 7

| Name | Kcy | Ksatu | Karo | Kiso | Kene | xxxx |
|---|---|---|---|---|---|---|
| CRK0071 | 124.2982 | 30.2213 | 6.1022 | 20.4044 | 22.6714 | |
| CRK0075 | 123.6416 | 30.3821 | 6.0959 | 20.0519 | 22.6293 | |
| CRK0098 | 123.3631 | 29.719 | 6.1168 | 21.0968 | 22.9267 | |
| CRK0102 | 122.6272 | 29.1777 | 6.1168 | 20.8441 | 23.3606 | |
| CRK0116 | 120.3105 | 29.5099 | 6.1134 | 21.0583 | 23.0629 | |
| HVY0068 | 144.4259 | 52.0212 | 5.9475 | 22.2027 | 13.5996 | |
| HVY0088 | 141.8204 | 47.8997 | 6.0091 | 23.0564 | 14.2034 | |
| HVY0093 | 143.0184 | 49.2953 | 5.9834 | 22.3627 | 14.0157 | |
| HVY0100 | 142.1157 | 43.480 | 5.9932 | 22.8488 | 14.183 | |
| HVY0106 | 143.3684 | 50.5179 | 5.9642 | 22.8179 | 13.8181 | |
| KER0072 | 114.2103 | 61.7041 | 5.8061 | 22.7724 | 13.9045 | |
| KER0076 | 112.7754 | 59.6154 | 5.8289 | 23.7607 | 14.191 | |
| KER0079 | 113.9722 | 56.389 | 5.8904 | 22.7878 | 14.299 | |
| KER0080 | 113.2538 | 57.5513 | 5.8681 | 23.0583 | 14.2554 | |
| KER0082 | 114.2399 | 62.3519 | 5.8108 | 23.6508 | 13.8976 | |
| LGT0067 | 130.8834 | 53.1217 | 5.9227 | 22.969 | 13.9002 | |
| LGT0087 | 129.4485 | 49.2411 | 5.9723 | 23.7952 | 14.4472 | |
| LGT0096 | 129.5402 | 48.6752 | 5.9809 | 23.382 | 14.5025 | |
| LGT0099 | 129.1717 | 48.8809 | 5.9775 | 23.6349 | 14.5186 | |
| LGT0105 | 129.4355 | 50.1752 | 5.9592 | 23.4217 | 14.267 | |

Table of aggregates

FIGURE 9

| Name | Absorbency | % Weight | Germ 1 | Germ 2 | Germ 3 | 4764 | 4760 | 4756 | 4752 | 4748 | 4744 | 4740 | 4736 | 4732 MDA | MDA | MDM |
|---|---|---|---|---|---|---|---|---|---|---|---|---|---|---|---|---|
| A0000001 | | | | | | 7.78E-06 | 1.29E-05 | 1.88E-05 | 2.42E-05 | 3.16E-05 | 4.42E-05 | 6.18E-05 | 8.01E-05 | 9.82E-05 | | 85.1 | 94.2 |
| A0000002 | | | | | | 8.08E-06 | 1.37E-05 | 1.96E-05 | 2.5E-05 | 3.18E-05 | 4.46E-05 | 6.09E-05 | 7.91E-05 | 9.8E-05 | | 85.3 | 94.7 |
| A0000003 | | | | | | 8.78E-06 | 1.52E-05 | 2.23E-05 | 2.97E-05 | 3.99E-05 | 5.53E-05 | 7.54E-05 | 9.66E-05 | 0.000112 | | 85 | 94 |
| A0000004 | | | | | | 7.46E-06 | 1.28E-05 | 1.81E-05 | 2.47E-05 | 3.29E-05 | 4.71E-05 | 6.55E-05 | 8.47E-05 | 0.000104 | | 85 | 93.5 |
| A0000005 | | | | | | 1.01E-05 | 1.59E-05 | 2.39E-05 | 3.28E-05 | 4.34E-05 | 5.93E-05 | 8.09E-05 | 0.000104 | 0.000123 | | 85.3 | 95.1 |
| A0000006 | | | | | | 5.49E-06 | 9.2E-06 | 1.41E-05 | 1.88E-05 | 2.54E-05 | 3.62E-05 | 5.18E-05 | 6.97E-05 | 9.06E-05 | | 84.4 | 92.8 |
| A0000007 | | | | | | 7.14E-06 | 1.21E-05 | 1.86E-05 | 2.41E-05 | 3.27E-05 | 4.63E-05 | 6.52E-05 | 8.49E-05 | 0.000104 | | 85 | 93.5 |
| A0000008 | | | | | | 1.03E-05 | 1.64E-05 | 2.4E-05 | 3.26E-05 | 4.39E-05 | 6.13E-05 | 8.42E-05 | 0.000109 | 0.000136 | | 85.5 | 95.1 |
| A0000009 | | | | | | 8.25E-06 | 1.19E-05 | 1.4E-05 | 1.62E-05 | 1.90E-05 | 2.56E-05 | 3.56E-05 | 4.34E-05 | 6.62E-05 | | 85.4 | 95 |
| 12G222 | 0.564 | | A0000003 | A0000006 | | 7.35E-06 | 1.36E-05 | 1.88E-05 | 2.49E-05 | 3.36E-05 | 4.7E-05 | 6.51E-05 | 8.5E-05 | 0.000105 | 84.73846 | 93.47603 |
| | 0.436 | | | | | | | | | | | | | | | |
| 12G011 | 0.654 | | A0000009 | A0000001 | | 8.09E-06 | 1.2E-05 | 1.57E-05 | 1.9E-05 | 2.4E-05 | 3.21E-05 | 4.47E-05 | 6E-05 | 7.25E-05 | 85.20638 | 94.72287 |
| | 0.346 | | | | | | | | | | | | | | | |
| 12G036 | 0.44 | | A0000008 | A0000004 | | 8.66E-06 | 1.43E-05 | 2.07E-05 | 2.81E-05 | 3.77E-05 | 5.33E-05 | 7.38E-05 | 9.54E-05 | 0.000116 | 85.21394 | 94.20281 |
| | 0.56 | | | | | | | | | | | | | | | |
| 13G038 | 0.747 | | A0000008 | A0000002 | A0000004 | 9.71E-06 | 1.57E-05 | 2.29E-05 | 3.06E-05 | 4.09E-05 | 5.7E-05 | 7.83E-05 | 0.000101 | 0.000126 | 85.46306 | 95.08502 |
| | 0.258 | | | | | | | | | | | | | | | |
| | -0.005 | | | | | | | | | | | | | | | |
| 13G035 | 0.5825 | | A0000008 | A0000005 | A0000003 | 1E-05 | 1.61E-05 | 2.38E-05 | 3.23E-05 | 4.33E-05 | 6E-05 | 8.22E-05 | 0.000106 | 0.000131 | 85.35181 | 94.97264 |
| | 0.3020 | | | | | | | | | | | | | | | |
| | 0.1155 | | | | | | | | | | | | | | | |
| 13G219 | 0.094 | | A0000004 | A0000005 | A0000007 | 7.43E-06 | 1.25E-05 | 1.81E-05 | 2.46E-05 | 3.28E-05 | 4.7E-05 | 6.54E-05 | 8.46E-05 | 0.000104 | 84.93829 | 93.49245 |
| | -0.00047 | | | | | | | | | | | | | | | |
| | 0.00647 | | | | | | | | | | | | | | | |

BROADENED SPECTRAL DATABANK E – with characterization

FIGURE 10

METHOD FOR DETERMINING THE ORIGIN OF A MIXTURE OF CONSTITUENTS BY SPECTRAL ANALYSIS

The present invention relates to a method for determining the origin of a mixture of constituents by spectral analysis. In particular, the present invention relates to a method for determining the concentration and the origin of raw gases and/or crude oils in a mixing zone after mixing by the transport of these raw gases and/or crude oils coming from at least two different sources of extraction, which method comprises a specific spectral analysis.

In order to reduce their cost, oil producers usually share their installations and equipment, in particular in the area of the transporting of gas and/or of oil. Therefore, it is well-known to transport mixtures of gas and/or oil coming from different sources of extraction, for example from different wells and/or from different oil fields.

However, it is also critical for oil producers to be able to determine in a precise and efficient manner the exact origin of these gases and/or oils after they are mixed.

US2010116991 concerns a method for measuring the concentration of biodiesel in a biodiesel-diesel homogeneous mixture using a measuring of an absorption peak in the infrared area which corresponds to the absorption peak of the carbonyl group (CO) which is present only in the biodiesel. This method requires a calibration stage consisting of making diesel/biodiesel mixtures in an entire range of concentrations and analyzing them in such a manner as to then be able to associate the concentration of biodiesel in the diesel with an absorption peak of the carbonyl group (CO).

U.S. Pat. No. 6,087,662 describes a method for measuring the concentration of asphaltenes in a charge of hydrocarbons by infrared spectroscopy. This method implies a method of chemical analysis of the content of asphaltenes of numerous known samples in order to establish databases which then allow the determination of the concentration of asphaltenes of new samples.

WO2011073855 describes this importance and claims a method for analysis in real time of the effect of the emplacement of the production well; the method consists in making spectroscopic measurements in situ in the vicinity of the emplacement of the well of a fluid produced from one or more of several drilling holes, which fluid comes from a mixture of at least a first component of a first production zone and of a second component from a second production zone and of estimating the real distribution of at least the first component as a function of the spectroscopic measurements in situ. The measuring in situ can be of several types, for example: (1) the absorption of the radiations of the lengths of electromagnetic waves in the ultraviolet range, visible and/or infrared, (2) the spectroscopic measuring of fluorescence by X-rays, (3) spectroscopic measurements by electromagnetic diffusion such as Raman spectroscopy, (4) spectroscopic measurements by magnetic resonance, and (5) spectroscopic measurements in the terahertz range.

The present invention has a similar objective in certain embodiments for determining in a precise and efficient manner the exact origin of gases and/or oils after they have been mixed.

Therefore, the present invention relates to a method for determining the concentration and the origin of gases and/or of oils in a mixing zone after mixing by the transporting of these gases and/or oils coming from at least two different origins, which method comprises a spectral analysis carried out in a range of wavelengths for each gas and/or oil coming from different origins, a spectral analysis carried out in the same range of wavelength for the gases and/or oils of the mixture a comparison stage among all the spectral analyses, and a stage for highlighting by means of this comparison among these spectral analyses a characterizing spectral range, preferably without referring to and/or without the least correlation with the chemical and/or physico-chemical properties of these gases and/or oils, which allows a discrimination among them of the different origins of these gases and/or oils and therefore a determination of the concentration and of the origin of each of the gases and/or oils in the mixture.

The origin of the gases and/or oils in the framework of the present invention can signify any sort of origin preceding the mixing stage of these gases and/or oils. In particular, and which is a preferred embodiment of the present invention, this origin is an origin of the extraction of this gas and/or oil.

The spectral analyses of the present invention are preferably carried out in the near infrared range ("NIR").

The spectral analyses according to the present invention are preferably the topological spectral analyses as explained in detail in the present specification.

The spectral analysis of each gas and/or oil coming from different origins can be carried out at any location before the mixing zone. By way of illustrative example, it is possible to cite the conduit for supplying this gas and/or oil, the extraction platform, the wellhead, or also the interior of the extraction well; for the spectral analysis carried out in situ (as, for example, the wellhead or the interior of the extraction well), an optical fiber can be used with advantage. This spectral analysis can be made in a continuous manner (for example, at the frequency of the measuring of the spectra) and/or preferably in a discontinuous manner (for example, at least once a day).

The spectral analysis of the mixture, which is therefore carried out in the same wavelength range as that of the gases and/or oils of different origins, can be carried out at any location downstream from the actual mixing. It is possible to cite by way of illustrative example any conduit for supplying this mixture of gases and/or oils. This spectral analysis can be made in a discontinuous manner (for example once a day) and/or preferably in a continuous manner (for example at the frequency of the measuring of the spectra).

By way of illustration, in order to highlight the characterizing and discriminating spectral range, it is possible to carry out, as described above in the specification, a statistical analysis of the spectra taken for each sample of a plurality of samples of gases and/or oils coming from different origins and for the gas and/or oil of the mixture.

According to an embodiment of the present invention the characterizing spectral range comprises at least one characterizing spectral data (characterizing spectral magnitude) and/or at least one characterizing spectral analysis and/or at least one bank of characterizing spectral data which discriminates among the different origins of the gases and/or oils.

The characterizing spectral range can be determined by any appropriate method of spectral analysis.

Note by way of example for spectral analysis the analyses of RMN, Raman, IR and/or UR/visible, preferably the (topological) spectral analysis in the near infrared ("NR").

According to a preferred embodiment of the present invention the spectral data is data measured by the same type of spectral analysis, preferably by means of the same type of spectrometer; this spectral data can be, for example, "spectra".

The characterizing spectral range can be determined by any appropriate method. By way of example, this range is determined by means of aggregates such as described hereinafter in the specification. The basic characteristic of the characterizing spectral range is that it discriminates among the different origins of gases and/or oils.

As already indicated, the spectral data is preferably data measured by the same type of spectral analysis, preferably by means of the same type of spectrometer; this spectral data can be, for example, any appropriate type of spectral magnitudes constituted by a corresponding bank of spectral data. These spectral magnitudes can be all types of signals characterizing the spectra, for example, the absorbencies, transmittances, reflectancies, etc . . . . ; the absorbencies or optical densities are the signals most commonly used. By way of example, the derivatives of the absorbencies or even any other measurement resulting from another type of mathematical treatment of these absorbencies can also be cited as signals.

The topological spectral analysis in the range of the near infrared ("NIR") proved to be particularly effective for allowing the characterization in the discrimination of the origins (of extraction) of the gases and/or oils transported in the mixture. Even if this does not constitute a preferred embodiment of the present invention, the determination of the characterizing spectral range can also be carried out by means of a analytical method by regression of the partial least squares (PLS).

The characterization of the origin according to the present invention can also consist of a determination and/or a prediction of any chemical, physical or physicochemical characteristic of the gases and/or oils and of their constituents and/or the identification of a type and/or family of the constituents.

The patent EP 0742900 of the Applicant constitutes the reference for the range of material of topological spectral analysis. It describes a method for the determination or the prediction of a value Px, of a property of a material X or of a property of a product resulting from a method stemming from this material or from the yield of this method, which method consists of measuring the absorption $D_ix$ of this material greater than a wavelength in the region of 600 to 2600 nm, of comparing the signals indicative of these absorptions or their mathematical functions with signals indicative of the absorptions Dim at the same wavelengths or their mathematical functions for a certain number of etalons S in a bank for which this property or yield P is known, and of choosing in the bank at least one and preferably at least 2 etalons Sm with the property Pm, which etalon Sm has the smallest average values of the absolute values of the difference at each wavelength i comprised among the signal for the material and the signal for the etalon Sm in order to obtain the value Px and to make the average of these properties or yields Pm when more than one etalon Sm is chosen.

The topological spectral analysis presents numerous advantages compared to classic, regressive mathematical activation means. The numeric methods described for the modeling of the physicochemical properties of substances based on spectral analysis are of a correlative nature and imply relationships with a regressive character among the property or properties studied. The analyses with multiple variables include the multilinear regression (MLR), the regression on a main component (PLR), the canonic regression and the regression of the partial least squares (PLS). In all these cases a relationship is sought among the property and the spectrum which can be linear but which is customarily quadric or with a greater algebraic form comprising coefficients of regression applied to each absorption. However, the establishing of any regression requires a progressive calibration since the approach is empirical and is not supported by a theory.

These techniques have disadvantages of which the main one is the need to establish a strong correlation among the spectrum and the property and their difficulty in treating the positive or negative synergy among the components contributing to this property. For example, in order to determine the chemical composition, for example LINA in a (linear, isoparaffinic, naphthenic, aromatic) in a charge of hydrocarbon feeding a catalytic reformer, the using of a PLS technique based on NIR spectra has been described. The model well suits the totality of calibration but the response of the models when pure hydrocarbons are added, for example, cyclohexane, is not satisfactory since the model predicts the variations of the content of isoparaffins and of inverse naphthenes of those found experimentally. Furthermore, there are other practical difficulties primarily due to the necessity of identifying samples of families having the same type of relationship among the spectra and the properties to be modeled. Therefore, the model can be limited, in particular with a non-linear relationship among the spectrum and the property. The precision of the model is reduced, especially when at the limits of the available data. The stability of the model is also a problem as well as the necessity during the addition of etalons of performing laborious revisions in order to obtain the new model, in particular when adjusting to a new charge feeding a procedure; therefore, the monitoring of 6 properties for 4 products exiting from one distillation unit requires 24 models of which each one must be modified for each modification of the feed charge not comprised in the calibration. Another major disadvantage encountered by these techniques appears when a point to be analysed is situated outside of the previously established model; it is then necessary to generate a new database and a new model by property, which renders this type of technique not only poorly reactive but also necessitates a number of very significant working hours.

It should be noted that the topological spectral analysis as such did not really develop from the patent EP0742900 of the Applicant. Nevertheless, the present invention also adds numerous improvements to this method of topological spectral analysis. The characteristics of this method of topological spectral analysis as well as its improvements and advantages will be described in detail in the following specification as well as in the examples, figures and claims. Other goals and advantages of the present invention will appear during the course of the following specification referring to embodiments which are given solely by way of indicative and non-limiting examples.

The understanding of this specification will be facilitated by referring to the joint FIGS. 1 to 10 attached and in which:

FIG. 2 shows an example of a bank of spectral data A,

Figure 4:
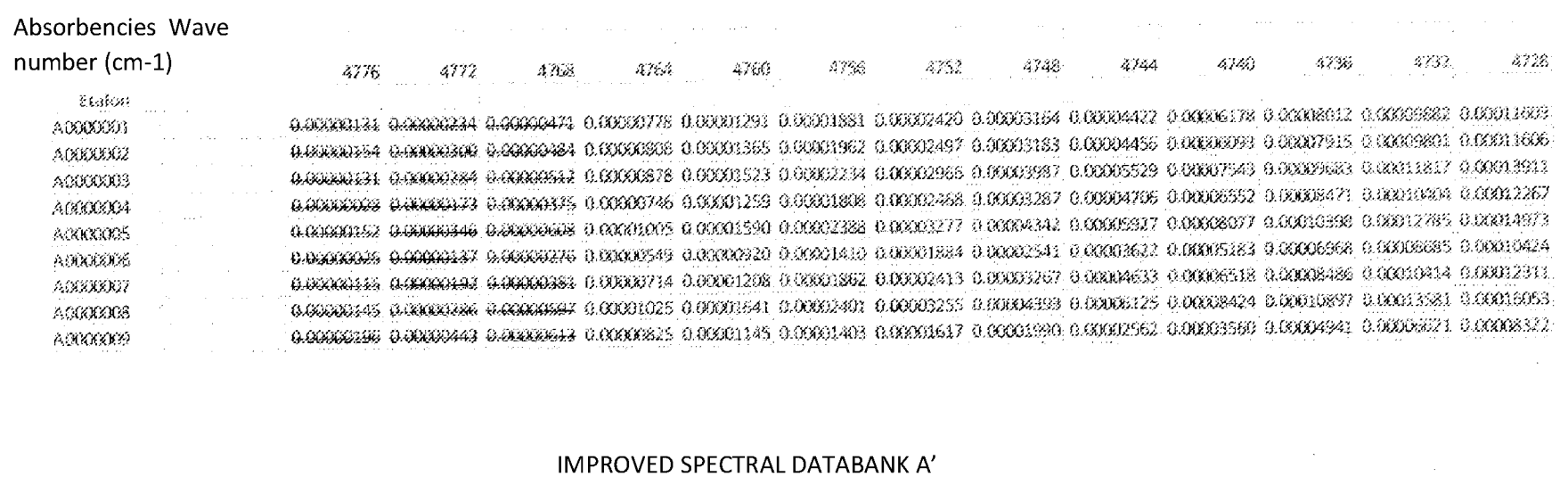
Figure 8:
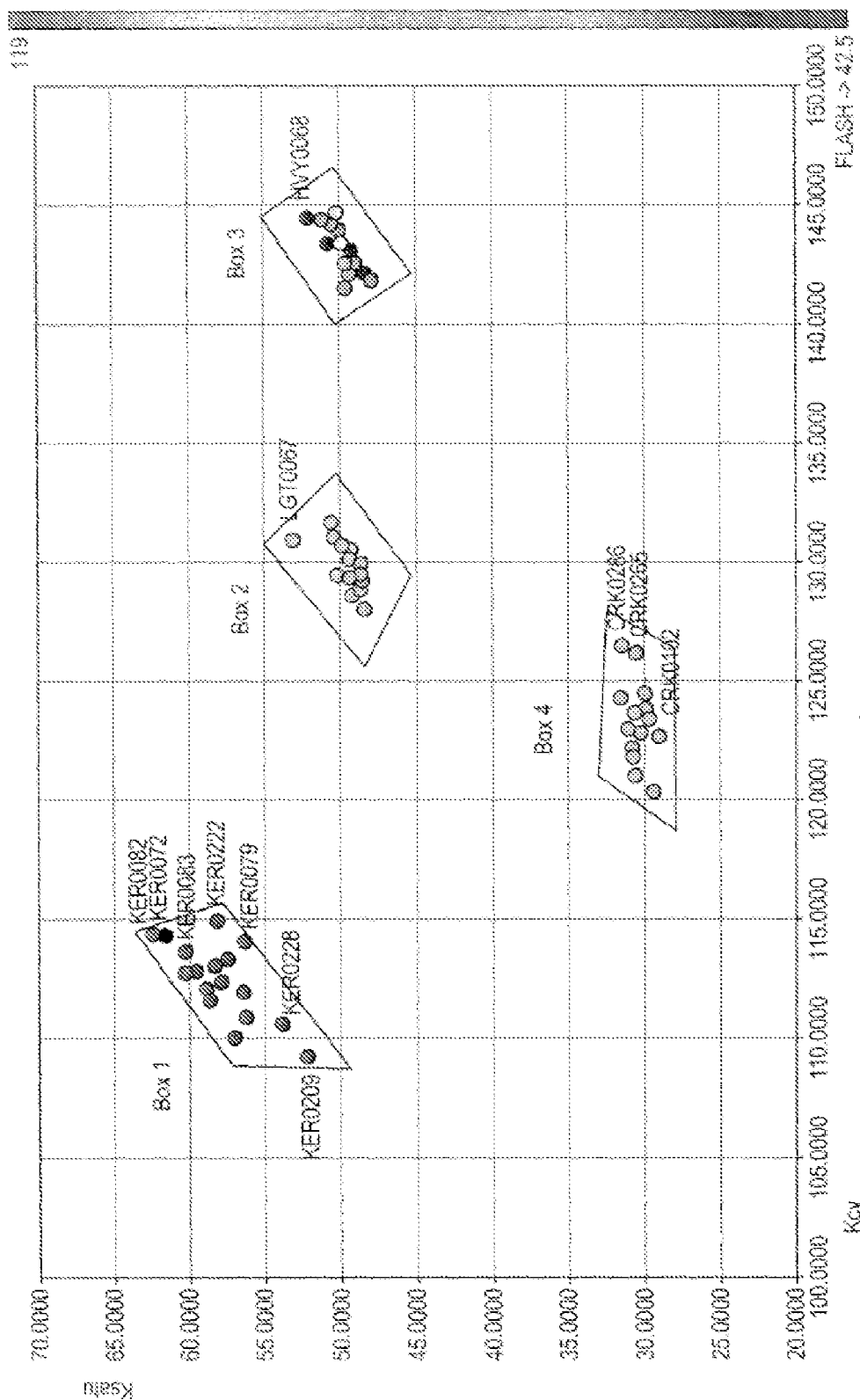

FIG. 3 shows an example of a bank of spectral data B (highlighting polluting wavelengths), FIG. 4 shows an example of an improved spectral databank A' (spectral databank A in which the spectral data corresponding to polluting wavelengths were eliminated), FIG. 5 shows an example of an enlarged spectral databank E (spectral databank A or A' in which intergerms were added), FIG. 6 shows an example of an enlarged spectral databank EE (spectral databank A and/or E in which extragerms were added), FIG. 7 shows an example of an enlarged spectral databank EEI (spectral databank E and/or EE in which extragerms' were added), FIGS. 8 and 9 respectively a graphic and a table representing discriminating aggregates, show and FIG. 10 shows a spectral databank of the type of that of FIG. 5 in which the measured characterizations of the etalons and calculation of the intergerms were added.

In particular, all the chemometric approaches of spectral analysis of the prior art require the establishing of a spectral databank constituted from a very significant initial number of samples and/or of etalons. Although the prior art sites constructions of spectral databanks based on at least 60 or at least 100 samples and/or etalons, all the examples describe banks constituted by a clearly greater number of samples. This number is even larger in the chemometric approaches using the regressive mathematical methods of which the databanks are constituted by hundreds, even thousands of samples and/or etalons. The present invention, in a particular embodiment, allows this prior requirement to be overcome, which opens up a considerable number of new applications, as demonstrated in the following.

Therefore, in a particular embodiment and at first, the method according to the present invention consists in the preparation of a bank of spectra and/or of spectral data of gases and/or of oils and of their constituents, preferably of an enlarged bank E of spectra and/or of spectral data for a limited number of available etalon materials (and therefore representing the gases and/or oils and/or their constituents as a function of their extraction origins).

Therefore, the present invention concerns more particularly the spectroscopy of the near infrared (NIR). In fact, the NIR spectroscopy has numerous advantages in comparison to other analytical methods, for example, in refineries, petrochemical or chemical sites as well as in all areas where the characterization of chemical products, for example, hydrocarbons, in particular fuels, and it can include a large number of repetitive applications with precision, rapidity and on line. Moreover, the region of the NIR among 800 and 2500 nm contains the totality of molecular information in the form of combinations and of harmonics of polyatomic vibrations.

In a first stage a selected type of spectral analysis is carried out on each of the etalons (representative of each of the gases and/or oils and/or of their constituents) and the bank A of spectra and/or of spectral data is then populated by registering the spectra in it (for example in numbered or digitized form), preferably the NIR spectra, with several wavelengths (or wave numbers), for example by a limited number of available etalon materials.

Figure 1:
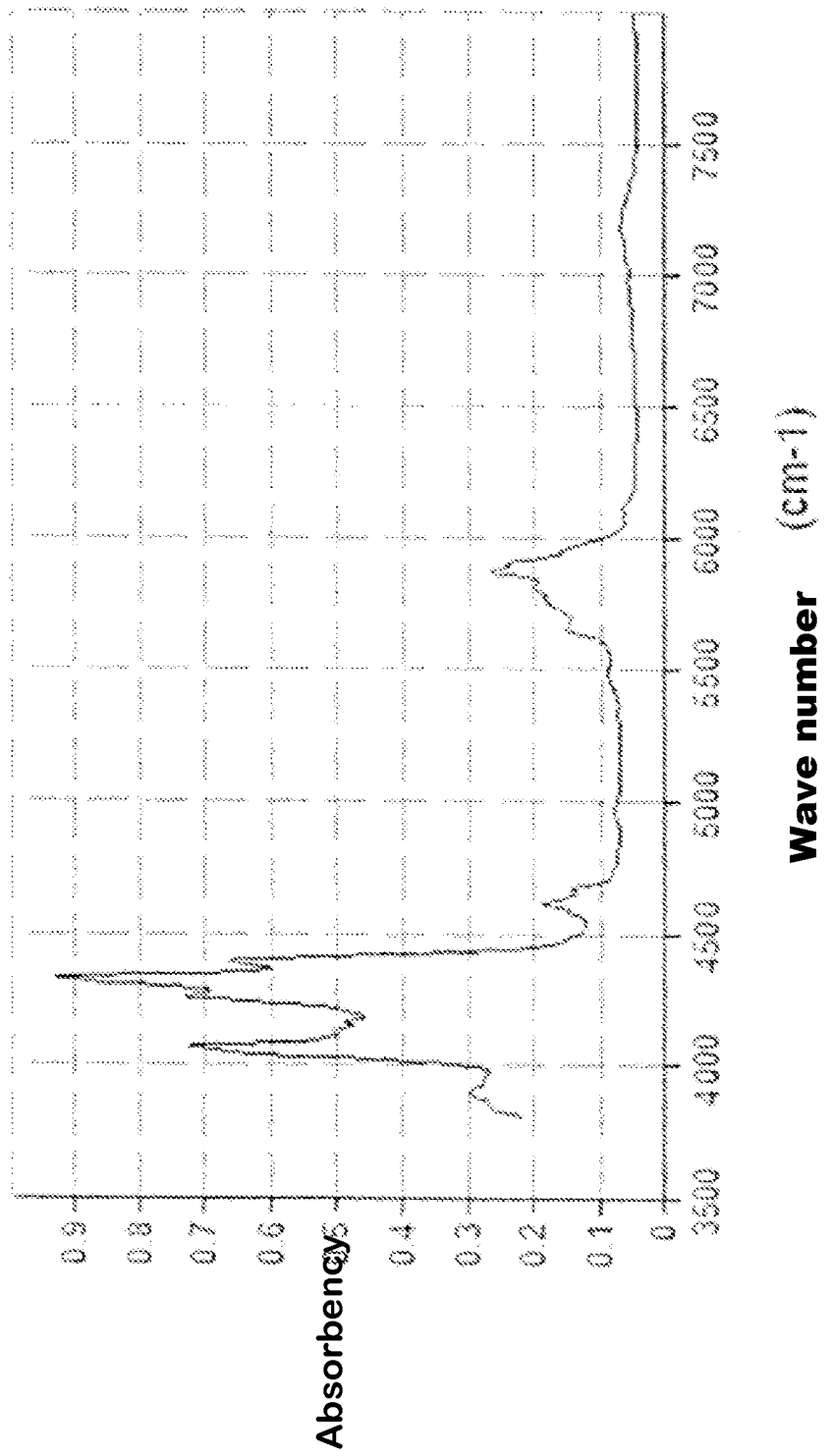
FIG. 1 shows the NIR spectrum of an etalon.
Figure 2:
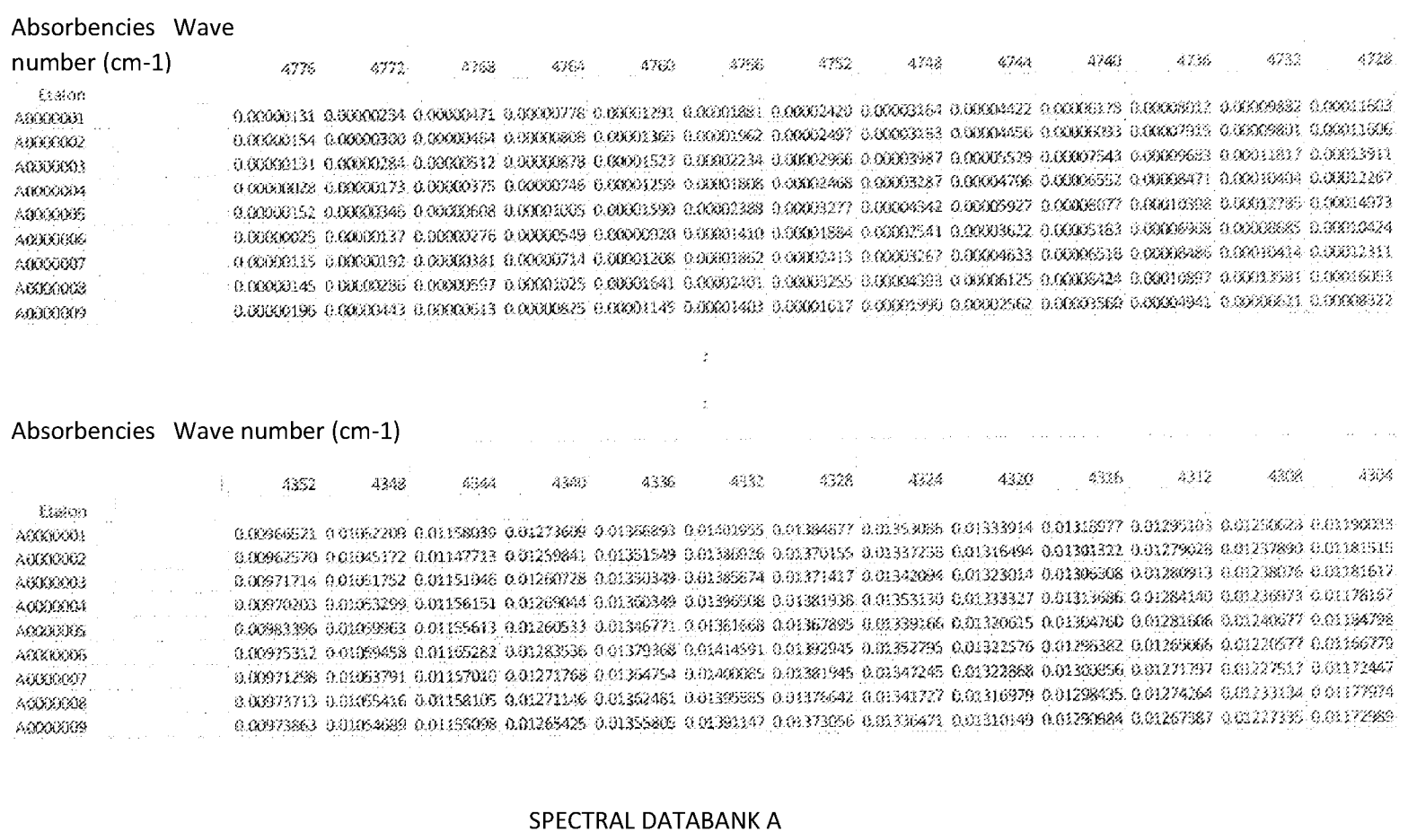

An example of the constitution and representation of this initial spectral databank is described by FIGS. 1 and 2.

FIG. 1 represents the NIR spectrum of an etalon on which it is possible to visualize as spectral magnitude the absorbency measured as a function of the wave number. Therefore, similar spectra are also established in an identical manner for each etalon. In the present example of representation, nine etalons were analyzed. Starting from the spectra, a table (the bank of spectral data A) is established of which a representative example is given in FIG. 2 for a limited number of wave numbers.

Therefore, it is possible to perceive in the table of FIG. 2 (which therefore corresponds to an abbreviated view—two parts of the table with different selected wave numbers) in the left column the references which allow the identification of the nine etalons and in the first line the value of the wave numbers or ranges of wave numbers; therefore, the table contents indicate the values of the spectral magnitudes (in the present case the absorbencies) which correspond to the couple "etalon reference/wave number". The spectral magnitudes can be all signal types characterizing the spectra, for example, the absorbencies, transmittances, reflectancies, etc . . . . ; the absorbencies or optical densities are the signals most commonly used. By way of example, the derivatives of the absorbencies or even any other measurement resulting from another type of mathematical treatment of these absorbencies can also be cited as signals.

The limited number of available etalons is generally dictated by the client and/or the final user, who wishes to use reactive and reliable control methods while limiting the necessity of having to dispose in advance of a large quantity of etalons and of having to carry out an analysis on them according to conventional methods.

A characteristic of the optional method according to the present invention is that it therefore allows eliminating the need dictated by the prior art of disposing of a very significant number of etalons. For example, the present invention allows the characterizing of a gas and/or oil sample (and its origin) from an available number of etalons lower than 100, even lower than 60 or even lower than 50. Very convincing results were even able to be obtained by the present invention from less than 40 available etalons, even less than 30 or even less than 20. A minimum of 10 available etalons is, however, preferred even if the present invention has already been successfully used with a minimum of 5 available etalons.

It is obvious for a person skilled in the art from the present invention, the specification made for it and the following claims that the spectra can be realized as a function of the wavelengths (and/or ranges of wavelengths) and/or as a function of the numbers of waves (and/or ranges of numbers of waves), because the number of waves is represented by the inverse of the wavelength.

For the present invention, its specification and the following claims, the etalons will also be qualified by "germs" ["G"], which two terms are interchangeable.

A second optional and preferred stage according to the present invention consists in the elimination of the "polluting" wavelengths and/or ranges of wavelengths of the spectral databank A. This stage consists of
1. repeating at least twice, preferably at least three times, more preferably at least five times the same spectral analysis as the one carried out during the first stage and which is to be carried out on at least one of the available etalons, preferably on at least two or even on the totality of these etalons;
2. constructing a spectral databank B from measures performed in point 1 above;
3. calculating for each etalon selected in point 1 above and for each wavelength and or range of wavelength (of the spectral databank A) the standard deviation ($\sigma$) of the measures registered in the databank B;
4. identifying in the databank B the wavelengths and/or wavelength range for which the standard deviation is greater than a predetermined value;
5. eliminating from the spectral databank A the measures corresponding to the wavelengths identified in point 4 above.

Therefore, according to a preferred embodiment of the present invention, the using of the above second stage allows the obtaining of an improved spectral databank A'; FIG. 4 shows an example of an improved spectral databank A'.

An example of a representation of the spectral databank B is illustrated in FIG. 3 by a table.

It can be seen that the same spectral analysis was repeated ten (10) times on the same sample and that the values of corresponding magnitudes were registered in the table. The three last lines of the table correspond respectively and successively to the value of the average spectral magnitude VGSmoyenne ("VGSm"), which corresponds to the sum of the values of the spectral magnitude divided by the number ("n") of analyses made (VGSm=[ΣVGS]/n), with n=10 in the present representation;

the standard deviation ("σ"), which corresponds to the difference among VGSmax and VGSmin in each column of the table;

the ratio (σ/(VGSm/100)) of which the value (in percentage) is calculated by dividing the standard deviation by the value of the average spectral magnitude, wherein the result is multiplied by one hundred.

Therefore, the last line of the table allows the identification in the databank B of the wavelengths and/or ranges of wavelengths for which the ratio (σ/VGSm/100) is greater than a predetermined value. According to an embodiment of the present invention, the columns (the wavelengths and/or ranges of wavelengths) are identified in table B for which the value of the ratios (σ/VGSm/100) is greater than 2% (preferably greater than 1.5% or even 1%); then, these columns, namely, the values of spectral magnitudes corresponding to the "polluting" wavelengths are eliminated from the databank A. The corresponding columns (that is, those whose wavelength and/or range of wavelengths are identical) will then be eliminated from the spectral database A. It should be noted that in the above examples the tables A and B constitute representations which are not true relationships among themselves; it should also be noted that the tables A and B were abbreviated in such a manner as to give them a visual representation; in reality, these tables comprise a multitude of columns representing the wavelengths and/or ranges of wavelengths extracted from the corresponding spectrum as detailed above in the specification.

Therefore, an example of a representation of the improved spectral databank A' is shown in FIG. 4.

An essential characteristic of this optional method according to the present invention consists in that the establishment of the improved spectral databank A' did not require at this stage referring to and/or the least correlation with the chemical and/or physical chemical properties of the etalons. In fact, the second stage is totally independent thereof.

A third preferred consecutive stage of this optional method according to the present invention consists in the actual enlarging of the spectral databank A (or of the improved spectral databank A'). This step consists in generating synthetic etalons (also called "intergerms" ["IG"]) from available etalons and their values of spectral magnitudes. For example, in order to generate these IG, it is possible to carry out combinations of several available etalons of the first stage above and to populate the spectral databank A (or the improved spectral databank A') by means of these combinations. These combinations can be made in a random manner or in an oriented manner such as described above in the text. These combinations can consist of any type of mathematical treatment applied to the spectral magnitude values of the G etalons. According to a preferred embodiment of the present invention this combination consists of a barycenter of the spectral magnitude values ("VGS") of at least two etalons. These combinations could be carried out, for example, among two, three or a greater number of starting, available etalons, preferably among all the starting, available etalons.

An example of a corresponding formula for generating a synthetic etalon (IG) starting from etalons G (to which the VGS correspond) is $$[\Sigma Ri \times VGSi]/[\Sigma Ri]$$

in which i is a whole number from 1 to the number of etalons G selected for this combination and R is a real number such as $$[\Sigma Ri] > 0, \text{ and}$$

$$|[\Sigma R^*i]|/[\Sigma Ri] < 0.3, \text{ preferably } < 0.15,$$

And with R* representing only the negative real numbers. This last formula can also be expressed as the absolute value of the sum of the negative real ones divided by the sum of all the real ones.

According to a preferred embodiment of the present invention, at least one of the Ri is a negative real one (R*).

By proceeding in this way, this therefore allows the broadening of the spectral databank A (or the improved spectral databank A') by means of synthetic etalons (also called "intergerms" or "IG"), and to therefore obtain a broadened spectral databank E.

According to a preferred embodiment of the present invention, when the number of etalons of the spectral databank A (or A') is "N", the number of intergerms IG is at least greater than 1.5 N, preferably greater than 2 N, more preferably greater than 5 N, even greater than 10 N.

A representative example of the enlarged spectral databank E is shown in FIG. 5 by a table. It can be seen there that the synthetic etalons (or intergerms "IG") were generated by mathematical combinations and that the values of corresponding spectral magnitudes were registered in the table E. The following can be seen by way of example in the table E (FIG. 5):

6 intergerms "IG" I2G022, I2G011, I2G036, I3G038, I3G025 and I3G019;

in the columns 3 to 5 the germs used to generate each of these intergerms;

in column 2, the ponderation applied to the germs selected for the calculation of the VGS of the intergerms (for example, for the calculation of the intergerm I2G036, a ponderation of (0.44 times the germ A0000008+0.56 times the germ A0000004)).

An essential characteristic of this optional method according to the present invention consists in that the establishing of the broadened spectral database E did not necessitate at this stage having to refer to and/or the least correlation with the chemical and/or physical chemical properties of the etalons. In fact, this broadening stage is totally independent thereof.

A fourth additional stage which is optional and preferred according to the present invention then consists of a supplementary broadening of the spectral databank A or of the broadened spectral databank E by means of another type of synthetic etalons which we will call "extragerms" ("EG"). This stage can prove to be particularly pertinent when the product to be analyzed contains a plurality of chemical compounds, for example, oil.

It consists in a first sequence in registering the spectral data of at least one spectrum corresponding to one (or several) of the chemical compounds of the gases and/or oils concerned (also called "Pole(s)"). Then, in a second sequence, an additional broadening of the spectral databank is made using these Pole(s) and combining them with the germs "G" (a combination of their spectral magnitude values VGS is therefore made).

This second sequence consists in generating synthetic etalons (also called "extragerms" ["EG"] from the Pole(s) and the available etalons and their spectral magnitude values. For example, in order to generate these EG, it is possible to make combinations of the Pole(s) and of several available etalons of the above first stage and to populate the spectral databank A and/or E by means of these combinations. There combinations can be made in a random manner or in an oriented manner such as described above in the text. These combinations can consist of any type of mathematical treatment applied to the spectral magnitude values of the etalons G and of the Pole(s). According to a preferred embodiment of the present invention, this combination consists of a barycenter of the spectral magnitude values ("VGS") of the etalons G selected and of the Pole(s). These combinations could be carried out, for example, among at least one Pole and one, two, three or a greater number of starting, available etalons, preferably with all the starting, available etalons. These combinations are preferably carried out with all the available Poles, preferably with all the Poles corresponding to all the chemical compounds constituting the analyzed product.

An example of a formula corresponding to the generation of a synthetic etalon of the EG type starting from Pole(s) and from etalons G (to which the VGS correspond) is $$[\Sigma Ri \times VGSi + \Sigma Rj \times VGSj]/[\Sigma Ri + \Sigma Rj]$$

in which i is a whole number ranging from 1 to the number of etalons G selected for this combination, j is a whole number ranging from 1 to the number of Pole(s) selected for this combination and R is a real number such as $$[\Sigma Ri + \Sigma Rj] > 0,$$

and $$|[\Sigma R^*i]|/[\Sigma Ri + \Sigma Rj] < 0.3, \quad (I)$$

preferably <0.15,
with R* representing only the negative real numbers, and, preferably, each Rj should be such that the ratio $$Rj/[\Sigma Ri + \Sigma Rj]$$

is always comprised among the opposite of the minimal content and the maximum content by percentage by weight of the Pole(s) j in the gases and/or oils.

The formula (I) above can also be expressed as being the absolute value of the sum of the negative real numbers "i" divided by the sum of all the real numbers. According to a preferred embodiment of the present invention, at least one of the Ri is a real negative number (R*).

Proceeding in this manner therefore allows the spectral databank A and/or E to be broadened by synthetic etalons "EG" ("extragerms") and to therefore obtain a broadened spectral databank EE. These Poles and their VGS can also be integrated in an optional manner into the spectral databank EE but this does not constitute a preferred embodiment according to the present invention.

According to a preferred embodiment of the present invention, when the number of etalons of the spectral databank A (or A') is "N" and the number of "Poles" is "M", the number of extragerms "EG" is at least greater than N×M, preferably greater than 1.5 N×M, preferably greater than 2 N×M.

According to an embodiment of the present invention the number of poles is lower than 15, for example lower than 10.

According to an embodiment of the present invention the number of poles is lower than 0.2 times the number etalons, for example lower than 0.1 times the number of etalons.

An example of representing the broadened spectral databank EE is shown in FIG. 6 by the table EE. It can show that the "Poles" as well as the generation of synthetic etalons "EG" (extragerms) by mathematical combinations and that the values of corresponding spectral magnitudes were registered in the table. The following can be seen by way of example in the table EE (FIG. 6):

six extragerms "EG" (MEG001 to MEG006);
  in column 2 ("Pole") the reference of the poles used (for example, the Pole PAL054 is a particular type of alkylate used in the composition of essences constituting the etalons of the databank);
  in column 3 the reference of the germs used to generate each of these extragerms;
  in column 4 the ponderation applied to the Poles (X)—therefore, the ponderation applied to the germs is (1-X). For example, for the calculation of the extragerm MEG001, a ponderation of (0.15 times the Pole PAL054+0.85 times the germ A0000009) is applied.

An essential characteristic of this optional method according to the present invention consists in that the establishment of the enlarged databank EE did not necessitate at this stage making reference to and/or making the least correlation with the chemical and/or physicochemical properties of the etalons. In fact, this broadening stage is totally independent thereof.

A fifth optional and preferred additional stage according to the present invention also consists of a supplementary broadening of the broadening of the spectral databank E and/or EE by means of another type of synthetic etalons which we will call "extragerms'" ("EG'"). This stage is again particularly pertinent when the product to be analyzed contains a plurality of chemical compounds, for example, oils.

It consists in a first sequence in registering the spectral data of at least one spectrum corresponding to one (or several) of the chemical compounds of the product (also called "Pole(s).").

Then, in a second sequence, an additional broadening of the spectral databank E or EE is made using these Pole(s) and by combining them with the intergerms "IG" (combination of their VGS).

This second sequence consists in generating synthetic etalons (also called "extragerms'" ["EG'"]) from the Pole(s) and the "intergerm" "IG" etalons (and optionally the germs "G") and from their spectral magnitude values. For example, in order to generate these EG', combinations of the Pole(s) and of several intergerms "IG" of the third stage above (and optionally of germs "G" of the first stage) can be made and the spectral databank E and/or EE can be populated by these combinations.

These combinations can be made in a random manner or in an oriented manner such as described above in the text. These combinations can consist of any type of mathematical treatment applied to the spectral magnitude values of the synthetic etalons (intergerms) "IG" and of the Pole(s) (and optionally of the germs "G").

According to a preferred of the present invention this combination consists of a barycenter of the spectral magnitude values ("VGS") of the intergerms IG and of the Pole(s) (and optionally of the germs "G"). These combinations among at least one Pole and one, two, three or a greater number of the "IG" of the third stage can be made, for example, preferably with all the "IG"; and optionally with at least one of the germs "G", preferably with all the germs "G". These combinations are made preferably with all the available Poles, preferably with all the Poles corresponding to all the chemical compounds constituting the product analyzed.

An example of a corresponding formula for the generation of a synthetic etalon of the EG' type starting from Pole(s) and from synthetic etalons IG (to which the VGS correspond) is $$[\Sigma Ri \times VGSi + \Sigma Rj \times VGSj + \Sigma Rk \times VGSk]/[\Sigma Ri + \Sigma Rj + \Sigma Rk]$$

in which k is a whole number ranging from 1 to the number of synthetic etalons IG selected for this combination, i is a whole number ranging from 0 (preferably 1) to the number of etalons G selected for this combination, j is a whole number ranging from 1 to the number of Pole(s) selected for this combination and R is a real number such as $$[\Sigma Ri + \Sigma Rj + \Sigma Rk] > 0,$$

and $$|[\Sigma R^*i] + [\Sigma R^*k]|/[\Sigma Ri + \Sigma Rj + \Sigma Rk] < 0.3, \quad (II)$$

preferably <0.15,
with Rk preferably always positive, with R* representing only the real negative numbers, ET preferably each Rj must be such that the relationship $$Rj/[\Sigma Ri + \Sigma Rj + \Sigma Rk]$$

is always comprised among the opposite of the minimum content and the maximum content by percentage of weight of the Pole(s) j in the product analyzed. The formula (II) above can also be expressed as being the absolute value of the sum of the real negative numbers "i" divided by the sum of all the real numbers. According to a preferred embodiment of the present invention at least one of the Ri is a real negative number (R*). Therefore, by proceeding in this manner, this allows the spectral databank E and/or EE to be broadened by means of the synthetic etalons "EG'" ("extragerms'") and therefore the obtention of a broadened spectral databank EEI. These Poles and their VCS can also be integrated in an optional manner into the spectral databank E, but this is not a preferred embodiment of the present invention.

According to a preferred embodiment of the present invention, when the number of synthetic etalons IG of the spectral databank E is "Z" and the number of "Poles" is "M", the number of extragerms' "EG'" is at least greater than Z×M, preferably greater that 1.5 Z×M, preferably greater than 2 Z×M. According to another preferred embodiment of the present invention, when the number of synthetic etalons IG of the spectral databank E is "Z", the number of germs G is N and the number of "Poles" is "M", the number of extragerms' "EG'" is at least greater than Z×M×N, preferably greater than 1.5 Z×M×N, preferably greater than 2 Z×M×N.

According to an embodiment of the present invention the number of poles is less than 15, for example, less than 10.

According to an embodiment of the present invention the number of poles is less than 0.2 times the number of etalons, for example, lower than 0.1 times the number of etalons.

An example of representing the broadened spectral databank EEI is illustrated in FIG. 7 by a table. It shows the "Poles" as well as the generation of the synthetic etalon "EG'" (extragerms') by mathematical combinations and that the values of corresponding spectral magnitudes were registered in the table. The table EEI (FIG. 7) shows by way of example:

Six extragerms' "EG'" (MEP001 to MEP006);

in column 5 ("Pole") the reference of the poles used (for example, the Pole PAL037 is a particular type of alkylate used in the composition of essences constituting the etalons of the databank);

in columns 2 to 4, the reference of the intergerms (combinations of germs) used to generate each of these extragerms;

in column 6 the ponderation applied. For example, for the calculation of the extragerm MEP004 a ponderation of [0.9 times an intergerm (corresponding to 0.306 times the germ A0000006-0.0530 times the germ A0000009+ 0.647 times the germ A0000002)+0.1 time the pole PAL037] is applied.

An essential characteristic of this optional method according to the present invention consists in that the establishment of the broadened spectral databank EEI did not require at this stage making reference and/or the least correlation with the chemical and/or physicochemical properties of the etalons. In fact, this broadening stage is totally independent thereof.

Therefore, the present invention also relates to a method of generating and optimizing a spectral databank which can serve in a method for the characterization of the origin of the gases and/or oils (and/or of the constituents) of different origins in a mixture of them by topological spectral analysis starting from a limited number of available etalons, which method consists in a first stage in carrying out the same spectral analysis on these etalons, and in constituting, starting from the spectra obtained, a spectral databank A with several wavelengths and/or ranges of wavelengths, characterized in a second optional stage in that the "polluting" wavelengths and/or ranges of wavelengths of the spectral databank A are eliminated from the spectral databank A and a second stage consisting 1. of repeating at least two times, preferably at least three times, more preferably at least five times the same spectral analysis as the one made during the first stage, which is to be made on at least one of the available etalons, preferably on at least two or even on the totality of the available etalons;

2. of constructing a spectral databank B from the measurements made in point 1 above;

3. of calculating for each etalon selected in point 1 above and for each wavelength and/or range of wavelength (of the spectral databank A) the standard deviations (σ) of the measurements registered in the databank B;

4. of identifying in the databank B the wavelengths and/or range of wavelength for which the standard deviation is greater than a predetermined value; and 5. of eliminating from the spectral databank A the measurements corresponding to the wavelengths identified in point 4 above and therefore obtaining an improved spectral databank A', and also characterized by a third preferable stage which consists in the broadening of the spectral databank A (or of the improved spectral databank A'), which stage consists in making combinations of several etalons of the first stage and of populating the spectral databank A (or the improved spectral databank A') by these combinations (called synthetic etalons or intergerms "IG") and therefore obtaining a broadened spectral databank E, and also characterized by a fourth consecutive, optional stage which consists of the broadening of the spectral databank E, which stage consists in a first sequence of adding to the broadened spectral databank E at least one spectrum corresponding to at least one of the chemical compounds (or several) of the gases and/or oils (and/or of their constituents) of different origins (also called "Pole(s)") and in a second sequence of making mathematical combinations of this Pole or of these Poles with at least one etalon G of the first stage and/or at least one of the etalons IG of the third stage and of populating the spectral databank E by these combinations (respectively called either synthetic extragerm etalons "EG" or synthetic extragerm' etalons "EG'") and therefore obtaining a broadened spectral database EE (or EEI).

After having constituted the spectral database (preferably broadened in conformity with the methodology developed above) for each of the gases and/or oils in the transported mixture, it is possible to highlight by comparison among these databanks (using, for example, any type of conventional mathematical analysis) a spectral characterizing range which discriminates among them the origins of these gases and/or oils and to therefore determine the origins and the specific ratios of the gases and/or oils in the final transported mixture starting from the broadened spectral databanks. By way of illustration of the mathematical analysis, the topological spectral analysis and/or the analysis by regression of the partial least squares (PLS) are cited; in order to permit the characterization and the discrimination of the origins (of extraction) of the gases and/or oils in the transported mixture.

According to a preferred embodiment of the present invention, before this characterization an additional intermediate stage consists in defining a method of effective discrimination permitting the highlighting of homogeneous subgroups of products that preferably obey the same types of property-spectra linkings as a consequence of a strong analogy of molecular structure.

The discrimination methods can be based exclusively on techniques of mathematical analysis (for example, factorial analyses and/or analyses of principal components). Although some of these mathematical methods can prove to be useful, the present invention preferably also uses at least one empirical stage to perform this type of discrimination, an empirical stage based on a visual analysis of the spectra (for example, of the etalons and/or of the above-mentioned poles); although this does not constitute a preferred embodiment of the present invention, this visual analysis could also be made on reconstituted spectra (starting from their calculated VGS) of the intergerms and/or extragerms. This empirical stage therefore allows the highlighting of very slight differences among the spectra in question, differences which, after verification, can prove to be synonymous with the existence of homogeneous subgroups of products even it was possible to think at the beginning that the totality of the population of the products was homogeneous. This discrimination technique therefore allows the highlighting of differences among the products even if the final user did not yet know about them.

By way of summary, an essential characteristic of the optional method of establishing the broadened spectral databank according to a preferred embodiment of the above-mentioned invention is that it is not necessary to make reference to and/or make the least correlation with the chemical and/or physicochemical properties of the etalons. According to a preferred embodiment of the present invention it is exactly the same for the discrimination stage described here.

Therefore, according to an optional embodiment of the present invention the characterization and discrimination stage consists in defining, starting from the (preferably broadened) spectral databank, aggregates (preferably at least two aggregates) of the spaces with n dimensions representing the combinations of these aggregates (preferably of the planes- or spaces with two dimensions—representing couples of aggregates), and corresponding spectral boxes. According to a preferred embodiment of the present invention these aggregates and/or these spaces with n dimensions represent combinations of these aggregates and/or the spectral boxes define the spectral area characterizing and discriminating origins of these gases and/or oils, which therefore allows the determination of the origins and the respective ratios of the gases and/or oils in the final transported mixture.

According to an embodiment of the present invention the discrimination method also comprises at least two particular preferred characteristics:

1. the fact that this method implies an iteration phase during which the effectiveness of the spectral box and therefore the pertinence of the selected aggregates are verified; and
2. the fact that the aggregates are constructed starting from at least a visual analysis of the course of the spectra which then allows the construction of the equations of the aggregates as a function of the VGS spectral magnitude values.

The aggregates are therefore defined as mathematical functions of the spectral magnitude values of the broadened spectral databank, allowing the regrouping and/or discriminating and/or separating of the product families (in this case of the different origins of these gases and/or oils) in the broadened spectral databank.

These aggregates can therefore be represented in a generic manner by the function Agg=f(VGSi).

According to a preferred embodiment of the present invention this function agrees with the equations of the type $$\frac{\sum_{k=1}^{n}\sum_{i=1}^{p} a_i W_i^\alpha W_k^\beta}{\sum_{i=1}^{q} a_i W_i^\alpha}$$

or preferably of the type $$\frac{\sum_{i=1}^{p} a_i W_i^\alpha}{\sum_{i=1}^{q} a_i W_i^\alpha}$$

in which
W represents the discriminating VGS spectral magnitude values,
a is real positive numbers,
p and q represent the selection of the VGS at the wavelengths and/or ranges of wavelengths pertinent for the discrimination stage, and
α and β are exponents comprised among ⅓ and 3.

As concerns the iteration phase during which the effectiveness of the spectral box and therefore the pertinence of the selected aggregates are verified, it is sufficient to add columns representing the equations of the discriminating aggregates to the pre-established spectral databank, to calculate the value of these aggregates for each of the etalons and/or intergerms and/or extragerms and/or poles of the spectral databank, and to make the graphic representations for them (preferably in the spaces with two dimensions per pair of aggregates), and to visualize in this manner if the discrimination properly led to the highlighting of the homogenous subgroups of products (in this case different origins of these gases and/or oils). This discrimination stage therefore allows dividing the spectral databank into several (at least two) distinct families (homogeneous subgroups of products; in this case different origins of these gases and/or oils), of preferably at least three distinct families.

By way of example, FIGS. 8 and 9 respectively show
- a graphic whose abscissa/ordinate axes correspond to two discriminating aggregates, and
- a table of corresponding values of which the columns represent several discriminating aggregates of which the two first ones served for the construction of the graphic (FIG. 8).

These figures clearly explain how several homogeneous subgroups of products can be highlighted (in this case different origins of these gases and/or oils); this allows the selection of the characterizing and discriminating spectral area.

The present invention therefore also concerns a method for the characterizing of a product (in this case different origins of these gases and/or oils) by topological spectral analysis.

The characterization of the product according to the present invention can consists of a determination and/or a prediction of every chemical, physical or physicochemical characteristic of this product.

According to a particular embodiment of the present invention the first stage was therefore characterized by the establishing of a spectral databank, preferably a broadened spectral databank as described in the present specification.

As already indicated above, the graphic representations of the databanks (tables) in the attached figures constitute abbreviated views because in reality these databanks comprise a multitude of columns representing the wavelengths and/or ranges of wavelengths (or as an equivalent, the wave numbers or range of wave numbers) extracted from the corresponding spectra.

According to an embodiment of the present invention the number of wavelengths selected can be from 2 to 1,000, for example from 5 to 200 or from 40 to 80.

The wavelengths selected can be at regular intervals such as 1 to 50 nm or every 10 to 50 nm or every 15 to 35 nm or every 1 to 5 nm or all nanometers; or they can be at irregular intervals, for example at intervals of 1 to 200 nm, for example from 1 to 100 or from 1 to 50 and in particular from 2 to 50 or from 4 to 50 or from 10 to 60 nm, which can be selected or random at the rate of a variation of the shape of the spectral curve at this wavelength, for example, a peak, a valley or a shoulder or even selected with chemical or statistical criteria such as factorial analysis. The wavelengths can be in the area of 600 to 20,000 nm, for example from 625 to 2,600 nm, for example from 800 to 2,600 nm, in particular from 1,500 to 2,600 or from 2,000 to 2,550 nm. The numbers of waves can be in the area of 16,600 to 500, for example from 16,000 to 3,840 cm-1, for example from 12,500 to 3,840 cm-1, in particular from 6,660 to 3,840 or from 5,000 to 3,900 cm-1; the corresponding frequencies in Hertz can be obtained by multiplying these wavelengths by $3 \times 10 (\exp)10$ cm/s.

Before being able to determine and/or predict the property of a sample (in the present case of a mixture of gases and/or oils of different origins), it is clearly necessary to measure the values of this property for the etalons and, optionally, for the poles. Therefore, according to an embodiment of the present invention the chemical, physical and/or physicochemical properties of the etalons (and optionally of the poles) are determined by means of conventional analytic techniques. By way of non-limiting example of conventional analytic techniques, chromatography in gaseous phase for the chemical compositions is cited. Although it is understood that the etalons are selected for covering the range in which the method is to be used, the present invention allows in a preferred embodiment to work with a limited number of etalons due to the methodology of broadening the spectral databank mentioned above.

Therefore, in a preferred embodiment of the present invention the values of the desired properties measured for these etalons (and optionally of the poles) are added to the spectral databank; when the spectral databank is broadened, the values of these properties for the synthetic, intergerm etalons (and optionally for the extragerms) are then calculated starting from the formulas which serve to generate these synthetic etalons; this calculation is made in a simple manner by replacing the values of the VGS spectral magnitudes by the measured values of these properties of the etalons (and optionally of the poles) used in the formulas (and optionally, for the extragerms, by the values already calculated for the intergerms). The final result, therefore, is a spectral databank constituted by a number of points (etalons and optionally intergerms, poles and extragerms) associated with the desired (measured and calculated) properties. An example of this (abbreviated view) is given in FIG. 10.

This concerns by way of illustration a broadened spectral databank E constituted by etalons (A) and by intergerms (IG). The table was completed by the characteristics of the gases and/or oils investigated, to wit, the values RON and MON (the investigated octane index (RON) and the octane index of the motor (MON)). These characteristics were therefore measured for the etalons and calculated for the intergerms.

In the specification of EP0742900 a comparison is then made of the signals, for example the absorptions (or their derivatives) for the unknown sample, with the signals, for example the absorptions (or their derivatives) at the same wavelength of the etalons, and the etalons having the smallest differences are selected. Then, the average of the properties of these selected etalons is made for determining the property of the unknown sample. Therefore, a spectrum calculated from the target product is reconstituted to which the characteristic (property) calculated in this manner corresponds.

According to a preferred embodiment of the present invention this comparison of signals is therefore not carried out on the entirety of the spectral databank but solely on the part of the spectral databank representative of the homogeneous subgroup to which the sample belongs. This part of the spectral databank is defined by preferably using the above-mentioned discrimination method (discriminating aggregates).

Then, the signals are prepared, for example the absorptions (or their derivatives or any other spectral magnitude values) for the unknown sample (sample preferably taken online in the transport conduit of the gases and/or oils in mixture), with the same signals and at the same wavelengths of the etalons and/or intergerms and/or extragerms and/or poles belonging to the same homogeneous subgroup, and the etalons and/or intergerms and/or extragerms and/or poles having the smallest differences are selected in the spectral databank.

Whatever the method used, in the following we will call the points close to the target product "close neighbors". Then, it is possible, for example, to make the average of the properties of these etalons and/or intergerms and/or extragerms and/or poles selected for determining the sought characteristic (property) of the unknown sample.

According to a particular embodiment of the present invention the close neighbors selected are those with the smallest average values of the absolute difference at each wavelength i among the spectral magnitude value (represented by way of example by the absorbency or a derivative of the latter) Wix for the target product (sample/unknown product) and the corresponding signal Wim for the close neighbor. The averages can refer, for example, to the average value of Wix−Wim (whatever its sign, namely, an absolute difference), or of (Wix−Wim)exp2. The average difference such as described is found for each close neighbor in the spectral databank for the type of product in question and the close neighbor with the smallest average differences is selected, namely, at least 1 but preferably 2, up to 1,000 of the smallest ones, for example, 2 to 100 or 2 to 20 but in particular 2 to 10 and especially 2 to 6 of the smallest ones. This selection of the closest neighbors can be made according to any known method, for example, the methods described in the specification of the patent EP0742900 (for example, by determining the proximity index) can be advantageously used.

According to a particular embodiment of the present invention the number of close neighbors can be equal to 1, preferably greater than or equal to 2, even more preferably greater than or equal to 3.

According to an embodiment of the present invention the number of close neighbors is lower than or equal to 50, for example lower than or equal to 20, even 10.

As was previously indicated, starting from the moment at which the "close neighbors" points were selected, it is easy to calculate the average of the property of these selected close neighbors (etalon and/or intergerms and/or extragerms and/or poles) for determining the property of the unknown sample (the target product). Therefore, a calculated spectrum of the target product was reconstituted to which the characteristic (property) calculated in this manner corresponds.

However, and this constitutes a preferred embodiment of the present invention, the Applicant discovered in unexpected manner a significant improvement of the precision and robustness of its method during the determination of the characteristic sought for (for example, a property) of a target product when the weighted average of the properties of these "close neighbors" points is carried out (whether they are etalons and/or intergerms and/or extragerms and/or poles), which ponderation is a linear or non-linear function which is inversely proportional to the distance among the sample ("the target product") and the "close neighbors" points selected; this ponderation can be represented, for example, by the formula $$POND = \frac{\frac{1}{di^\alpha}}{\sum_{1}^{n} \frac{1}{di^\alpha}}$$

in which $\alpha$ is a positive number preferably comprised among 0.5 and 1.5, di is the distance among the target product and the close neighbor i, and n is the total number of close neighbors.

Therefore, a ponderation of this type is applied to the measured (and optionally calculated) properties of the "close neighbors" in order to obtain the property of the target product.

Therefore, a calculated spectrum of the target product is reconstituted to which the characteristic (property) calculated in this manner corresponds.

In other words, the calculation of the characteristic Z of the target product is made by virtue of the corresponding characteristics Zi of the close neighbor points while giving the characteristics of these close neighbor points a weight that is all the more important in this calculation the closer they are to the target product.

Therefore, the present invention also relates to a method of characterizing a target product comprising the following stages:

1. The constituting of a spectral databank comprising samples, their spectra and their measured characteristics ("CAR", for example, the property "P"),
2. The spectral analysis of the target product and comparison of the spectrum obtained (Spectrum PC) with the spectral data of the databank,
3. The identification of the "close neighbor" points of the target product, and
4. The calculation by topology of the characteristic of the target product (CARpc/top, for example, the property Ppc/top) as a function of the corresponding characteristics of the close neighbor points, characterized in that the calculation of stage 4 is based on a ponderation associated with the inverse of the distance among the target product and the close neighbor points.

The method of the invention can be used to determine more than one property P simultaneously, for example, at least 2, in particular from 1 to 30, for example, 2 to 10 properties simultaneously. Obviously, names of different etalons can be selected for each property.

According to another preferably embodiment of the present invention the Applicant discovered a particularly effective method.

This method consists in combining one of the above-cited topological methods of characterizing the target product with any mathematical model different from topological methods (preferably a regressive model) and allowing the target product to be characterized starting from spectral magnitude values VGS (for the same property).

Therefore, this method implies the previous constitution of a mathematical model which allows the calculation of the properties of the products as a function of the spectral magnitude values (VGS) of the databank, preferably a regressive model (for characterizing the product starting from the previously established spectral databank); this spectral databank can be either the databank A cited above or preferably the databank A', E, EE or EEI, or a selection of these banks. This databank is preferably the same as the one which served for the topological method.

This alternative method for characterizing a target product comprises the following stages:
1. The constituting of a spectral databank comprising samples, their spectra and their measured characteristics ("CAR", for example, the property "P"),
2. The spectral analysis of the target product and comparison of the spectrum obtained (Spectrum PC) with the spectral data of the databank,
3. The identification of the "close neighbor" points of the target product,
4. The calculation by topology
   4.1. of the characteristic of the target product (CARpc/top, for example, the property Ppc/top), and
   4.2. of its spectrum calculated in this manner (spectrum PCcalc),
5. The establishment, starting from the spectral databank, of a mathematical model allowing the calculation of the characteristic of a product starting from the spectral databank (CAR/mod, for example, property P/mod),
6. The calculation of the characterization of the target product PC following the following formula CARpc=CARpc/top+[CARpc/mod−CARpccalc/mod] in which
   CARpc is the calculated value of the characteristic of the researched target product,
   CARpt/top is the value calculated by topology (close neighbor points) of the characteristic of the target product,
   CARpc/mod is the value calculated by the mathematical model of the characteristic of the target product, and
   CARpccalc/mod is the value calculated by the mathematical model of the characteristic of the target product calculated (by means of the spectral data obtained under point 4.2).

The characterization of a product according to the present invention can therefore consist of a determination and/or of a prediction of every chemical, physical or physicochemical characteristic of this product and/or of the identification of a type and/or family of products.

It is possible, for example, to determine the presence of individual chemical compounds in a composition as well as their concentrations; it is also possible to determine every type of useful properties of these gases and/or oils.

It should be evident for a person skilled in the art that the present invention allows embodiments under numerous other specific forms without departing from the scope of the application of the invention such as claimed. Therefore, the present embodiments should be considered as illustrations but can be modified within the scope defined by the extent of the attached claims.

The invention claimed is:

1. A method for determining concentration and origin of gases and/or of oils in a mixing zone after mixing by transporting of these gases and/or oils coming from at least two different origins, which method comprises
   a spectral analysis carried out in a range of wavelengths for each gas and/or oil coming from different origins,
   a spectral analysis carried out in the same range of wavelengths for the gases and/or oils in a mixture,
   a comparison stage among all the spectral analyses,
   and a stage for highlighting by means of this comparison among these spectral analyses from a characterizing spectral range without referring to and/or without a least correlation with chemical and/or physicochemical properties of these gases and/or oils, which allows a discrimination among them of the different origins of these gases and/or oils and therefore a determination of concentration and of origin of each of the gases and/or oils in the mixture, wherein the characterizing spectral range is determined by topological spectral analysis and the spectral analyses are performed in the near infrared range ("NIR") and wherein a selection of close neighbors of the gases and/or oils in the mixture is performed in the characterizing spectral range.

2. A method for determining concentration and origin of gases and/or of oils according to claim 1 wherein the origin constitutes an origin of extraction of the gases and/or oils.

3. A method for determining concentration and origin of gases and/or of oils according to claim 2 wherein origins of the extraction of the gases and/or oils are wells and in that the spectral analyses of the gases and/or oils coming from these wells are carried out on an extraction platform and/or on a wellhead, and/or inside the well.

4. A method for determining concentration and origin of gases and/or of oils according to claim 3 wherein the spectral analyses are carried out in situ using an optical fiber.

5. A method for determining concentration and origin of gases and/or of oils according to claim 1 wherein the spectral analyses come from spectra obtained by a same type of spectrometer.

6. A method for determining concentration and origin of gases and/or of oils according to claim 1 wherein the stage of highlighting a characterizing spectral range comprises an empirical stage based on a visual analysis of the spectra.

7. A method for determining concentration and origin of gases and/or of oils in a mixing zone after mixing by transporting of these gases and/or oils coming from at least two different origins, which method comprises:
   a spectral analysis carried out in a range of wavelengths for each gas and/or oil coming from different origins,
   a spectral analysis carried out in the same range of wavelengths for the gases and/or oils in a mixture,
   a comparison stage among all the spectral analyses,
   and a stage for highlighting by means of this comparison among these spectral analyses from a characterizing spectral range without referring to and/or without a least correlation with chemical and/or physicochemical properties of these gases and/or oils, which allows a discrimination among them of the different origins of these gases and/or oils and therefore a determination of concentration and of origin of each of the gases and/or oils in the mixture, wherein the characterizing spectral range is determined by topological spectral analysis and the spectral analyses are performed in the near infrared range ("NIR"), wherein a selection of close neighbors of the gases and/or oils in the mixture is performed in the characterizing spectral range and wherein a distance between the close neighbors of the gases and/or oils in the mixture in the characterizing spectral range determines concentration and origin of each of the gases and/or oils in the mixture.

* * * * *